(12) United States Patent
Schneider et al.

(10) Patent No.: US 8,257,366 B2
(45) Date of Patent: Sep. 4, 2012

(54) DIGITAL SUTURE FIXATION SYSTEM

(75) Inventors: Scott Schneider, Charlotte, NC (US); Sarah J Deitch, Minneapolis, MN (US); Emily Daley, Brooklyn Center, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 12/912,788

(22) Filed: Oct. 27, 2010

(65) Prior Publication Data
US 2011/0196386 A1    Aug. 11, 2011

(51) Int. Cl.
*A61B 17/10* (2006.01)
(52) U.S. Cl. ...................................................... 606/139
(58) Field of Classification Search .................. 606/224, 606/232; 223/101; 2/21
See application file for complete search history.

(56) References Cited

U.S. PATENT DOCUMENTS

| | | | |
|---|---|---|---|
| 2,415,957 A * | 2/1947 | McCormack | 223/101 |
| 4,244,375 A | 1/1981 | Farrar et al. | |
| 5,027,433 A | 6/1991 | Menadier et al. | |
| 5,224,948 A | 7/1993 | Abe et al. | |
| 5,320,629 A | 6/1994 | Noda et al. | |
| 5,364,408 A | 11/1994 | Gordon | |
| 5,458,609 A | 10/1995 | Gordon et al. | |
| 5,507,041 A * | 4/1996 | Wright | 2/21 |
| 5,540,704 A | 7/1996 | Gordon et al. | |
| 5,562,686 A | 10/1996 | Sauer et al. | |
| 5,571,119 A | 11/1996 | Atala | |
| 5,575,800 A | 11/1996 | Gordon | |
| 5,578,044 A | 11/1996 | Gordon et al. | |
| 5,662,664 A | 9/1997 | Gordon et al. | |
| 5,700,272 A | 12/1997 | Gordon et al. | |
| 5,713,910 A | 2/1998 | Gordon et al. | |
| 5,728,113 A | 3/1998 | Sherts | |
| 5,728,135 A | 3/1998 | Bregen et al. | |
| 5,741,277 A | 4/1998 | Gordon et al. | |
| 5,741,279 A | 4/1998 | Gordon et al. | |
| 5,925,064 A | 7/1999 | Meyers et al. | |
| 5,938,668 A | 8/1999 | Scirica et al. | |
| 6,048,351 A | 4/2000 | Gordon et al. | |
| 6,071,289 A | 6/2000 | Stefanchik et al. | |
| 6,102,920 A | 8/2000 | Sullivan et al. | |

(Continued)

FOREIGN PATENT DOCUMENTS

WO    0112084    2/2001

(Continued)

OTHER PUBLICATIONS

Office Action mailed on Feb. 13, 2012 in U.S. Appl. No. 12/702,315.

*Primary Examiner* — Melanie Tyson
(74) *Attorney, Agent, or Firm* — Coloplast Corp., Coloplast A/S; Daniel G. Chapik; Nicholas R. Baumann

(57) ABSTRACT

A digital suture fixation system includes an anchor, an introducer that is attachable to a finger of a person such that at least a distal tip of the finger is available to palpate tissue and identify a landmark within a patient, and a delivery device attached to the introducer. The anchor is removably attached to the delivery device. The anchor is exposed on an exterior of the delivery device and the delivery device is positioned to allow the finger to push the anchor into the landmark.

4 Claims, 6 Drawing Sheets

U.S. PATENT DOCUMENTS

| | | |
|---|---|---|
| 6,332,888 B1 | 12/2001 | Levy et al. |
| 6,334,446 B1 | 1/2002 | Beyar |
| 6,346,111 B1 | 2/2002 | Gordon et al. |
| 6,475,135 B1 | 11/2002 | Levy |
| 6,478,791 B1 | 11/2002 | Carter et al. |
| 6,592,625 B2 | 7/2003 | Cauthen |
| 6,719,764 B1 | 4/2004 | Gellman et al. |
| 6,730,110 B1 | 5/2004 | Harari et al. |
| 6,893,448 B2 | 5/2005 | O'Quinn et al. |
| 6,936,054 B2 | 8/2005 | Chu |
| 6,984,247 B2 | 1/2006 | Cauthen |
| 6,997,932 B2 | 2/2006 | Dreyfuss et al. |
| 7,004,970 B2 | 2/2006 | Cauthen, III et al. |
| 7,033,370 B2 | 4/2006 | Gordon et al. |
| 7,041,111 B2 | 5/2006 | Chu |
| 7,048,749 B2 | 5/2006 | Kortenbach et al. |
| 7,052,516 B2 | 5/2006 | Cauthen, III et al. |
| 7,060,077 B2 | 6/2006 | Gordon et al. |
| 7,118,583 B2 | 10/2006 | O'Quinn et al. |
| 7,122,039 B2 | 10/2006 | Chu |
| 7,189,235 B2 | 3/2007 | Cauthen |
| 7,232,448 B2 | 6/2007 | Battles et al. |
| 7,442,198 B2 | 10/2008 | Gellman et al. |
| 2003/0023250 A1 | 1/2003 | Watschke et al. |
| 2003/0078604 A1 | 4/2003 | Walshe |
| 2003/0078617 A1* | 4/2003 | Schwartz et al. ............ 606/230 |
| 2003/0236549 A1 | 12/2003 | Bonadio et al. |
| 2004/0181243 A1 | 9/2004 | Chu et al. |
| 2004/0193211 A1 | 9/2004 | Voegele et al. |
| 2004/0236356 A1 | 11/2004 | Rioux et al. |
| 2005/0199249 A1 | 9/2005 | Karram |
| 2005/0222589 A1 | 10/2005 | Chu |
| 2005/0288708 A1 | 12/2005 | Kammerer et al. |
| 2006/0041263 A1 | 2/2006 | Chu et al. |
| 2006/0224184 A1 | 10/2006 | Stefanchik et al. |
| 2006/0293699 A1 | 12/2006 | Robertson |
| 2007/0021649 A1 | 1/2007 | Nowlin et al. |
| 2007/0055095 A1 | 3/2007 | Chu et al. |
| 2007/0225815 A1 | 9/2007 | Keith et al. |
| 2007/0239208 A1* | 10/2007 | Crawford ...................... 606/232 |
| 2007/0239280 A1 | 10/2007 | Keith et al. |
| 2007/0270890 A1 | 11/2007 | Miller |
| 2008/0071295 A1 | 3/2008 | Baxter et al. |
| 2008/0082105 A1 | 4/2008 | Chu |
| 2008/0091220 A1 | 4/2008 | Chu |
| 2008/0103351 A1 | 5/2008 | Montpetit et al. |
| 2008/0109015 A1 | 5/2008 | Chu et al. |
| 2008/0269782 A1 | 10/2008 | Stefanchik et al. |
| 2009/0023982 A1 | 1/2009 | Karram |
| 2009/0105743 A1 | 4/2009 | Chu |
| 2010/0174134 A1* | 7/2010 | Anderson et al. ............... 600/37 |

FOREIGN PATENT DOCUMENTS

| | | |
|---|---|---|
| WO | 2008147555 A2 | 12/2008 |
| WO | 2009075933 | 6/2009 |
| WO | 2011047685 | 4/2011 |

* cited by examiner

DIGITAL SUTURE FIXATION SYSTEM

BACKGROUND

Intracorporeal suturing of tissue during surgery presents challenges to the surgeon in that the surgeon is called upon to manipulate one or more suturing instruments within the confines of an incision formed in the patient's body. In some cases, the surgeon will use his/her finger(s) to dissect tissue or separate tissue along tissue planes to form a space within the tissue that allows the surgeon to palpate and identify a desired target location for placement of a suture. Often, the space formed in the dissected tissue is opened until it is large enough to receive both the surgeon's finger(s) and the suturing instrument(s). The space provides access to the identified target location where it is desired to place the suture. However, the intracorporeal target location is often disposed at an angle that is difficult to reach and can have a depth that precludes visualization of the target location. Delivering surgical instruments to the target location is challenging when the target location cannot be visualized by the surgeon.

SUMMARY

One aspect provides a digital suture fixation system. The system includes a suture assembly having an anchor, an introducer that is attachable to a finger of a person such that at least a distal tip of the finger is available to palpate tissue and identify a landmark within a patient, and a delivery device attached to the introducer. The anchor is removably attached to the delivery device. The anchor is exposed on an exterior of the delivery device and the delivery device is positioned to allow the finger to push the anchor into the landmark.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
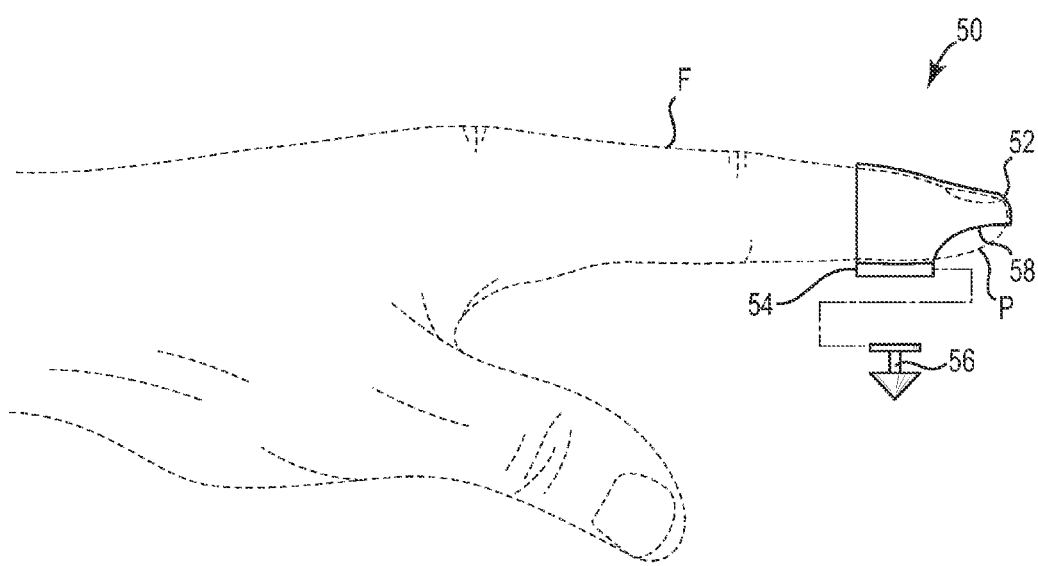
FIG. 1 is a side view of a digital suture fixation system including an introducer and an anchor delivery device according to one embodiment.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

A finger cot covers, at most, one finger. One such finger cot is a thimble that covers only a portion of the finger, for example a distal portion of the finger. Another example of a finger cot is a flexible sleeve that covers a distal portion of the finger. In contrast, a glove covers all five fingers and a portion of the hand up to at least the wrist.

One embodiment provides a digital suture fixation system having an introducer that is attachable to a finger of a person and a delivery device attached to the introducer. The introducer is configured to allow the finger to palpate and identify a landmark within a patient and the delivery device is configured to insert an anchor or a suture attached to an anchor into the landmark. Thus, the surgeon's finger delivers the anchor/suture such that the space formed in the dissected tissue to locate the landmark need not be so large as to accommodate a separate suturing instrument.

In this specification "configured to allow the finger to palpate and identify a landmark" means that the finger has a level of sensitivity that allows the person to discriminate tissue boundaries and/or tissue layers. For example, oftentimes the person is palpating a location inside a patient that is not within view and embodiments of the digital suture fixation system provide an introducer that attaches to the person's finger while allowing the finger to sense and identify the tissue the person is touching. That is to say, the introducer does not diminish the sensitivity of at least the pad of the palpating finger. In one embodiment, the introducer includes a polymer thin-walled section having a wall thickness of less than about 0.005 inches that is suited for providing digital dexterity. In one embodiment, the introducer includes a window that allows the finger to directly contact the tissues that are palpated.

Embodiments provide a digital suture fixation system that is configured to be donned over a finger of a surgeon to allow the finger to palpate and identify a landmark within the patient, where the system includes a delivery device configured to insert an anchor at the identified landmark. Other embodiments provide a digital suture fixation system having a thimble-like device that is configured to be affixed to a finger of a surgeon and yet allow the finger to palpate and identify a landmark within the patient.

Embodiments provide a digital suture fixation system that allows the surgeon to use the same finger(s) that were used to dissect tissue and identify the target location to also place the anchor/suture. Since the finger both palpates the tissue and places the anchor/suture, the space formed in the dissected tissue need not be opened to be large enough to receive other suturing instrument(s). Since the finger has already been employed to identify the target landmark, the subsequent location of the target landmark is relatively easy, even if the intracorporeal target location is disposed at an angle that is difficult to reach with instruments.

FIG. 1 is a side view of a digital suture fixation system 50 attached to a finger F according to one embodiment. System 50 includes an introducer 52 that is attachable to the finger F, a delivery device 54 that is attached to introducer 52, and an anchor 56 that is removably attachable to deliver device 54.

The intracorporeal suturing of tissue often includes the surgeon using one or more fingers to dissect tissue from tissue planes. In one embodiment, introducer 52 is provided with a window 58 that is formed on a distal end portion to allow a finger pad P of the finger F to be exposed (uncovered) to palpate tissue of the patient and identify a landmark for the placement of anchor 56. Surgeons rely upon their well developed dexterity to palpate and identify landmarks of a patient, and this is particularly the case when the surgeon is unable to visually view the landmark site. One embodiment of system 50 provides a window 58 that is sized to expose the pad P of the finger to allow the pad P to directly contact the tissue of the patient.

As an example of the use of system 50, in one embodiment the surgeon forms an incision in the patient, for example to access to pelvic floor. Thereafter, the surgeon places introducer 52 over the finger F and enters the incision to dissect tissue to locate a desired landmark within the patient. Having located the landmark within the patient, the surgeon removes the finger F from the patient and attaches anchor 56 to the delivery device 54. Subsequently, the surgeon will retrace the intracorporeal pathway into the patient with the finger F having the introducer 52 in the anchor 56 attached to the delivery device 54 for placement of anchor 56 into the landmark. As described below, one or more anchors 56 are employed to repair or support the pelvic floor with the appropriate use of support material or suture line as determined by the surgeon during the surgery. In one embodiment, anchor 56 is pre-attached to the delivery device 54.

It is to be understood that the finger F of the surgeon could be enclosed within a glove, and the introducer 52 is suited for donning over the glove that encloses the finger F.

Figure 2:
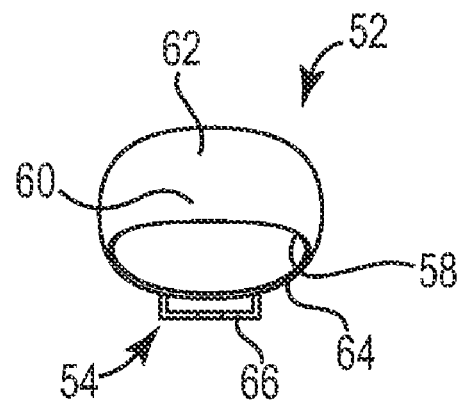
FIG. 2 is a front view of the introducer illustrated in FIG. 1.

FIG. 2 is a front view of introducer 52. In one embodiment, introducer 52 includes a distal end 60 formed by the intersection of a top surface 62 and a bottom surface 64. In one embodiment, window 58 is formed at the distal end 60 between the top surface 62 and the bottom surface 64 of the introducer 52. As illustrated in FIG. 1 and FIG. 2, in one embodiment introducer 52 is provided as a finger cot that is configured to snuggly fit over the finger F of the surgeon (or the finger F of the surgeon that is enclosed within a glove).

Delivery device 54 is attached to the bottom surface 64 of introducer 52. In one embodiment, delivery device 54 is provided as a U-shaped dock having a shelf 66 that is spaced a distance away from the bottom surface 64. The anchor 56 (FIG. 1) is configured to slide into the delivery device 54 and be frictionally captured between the shelf 66 and the bottom surface 64 of the introducer 52.

The introducer 52 is suitably fabricated from polymers that are configured to elastically constrict over a finger of the surgeon. Some of the suitable polymers for fabricating the introducer 52 include polybutylene, polynitrile, polyurethane including polyurethane from the family of elastic polymers sold under the tradename KRATION, silicone, or block copolymers. In one embodiment, introducer 52 is formed from a malleable metal core, for example aluminum, that is over molded with silicone.

Figure 3:
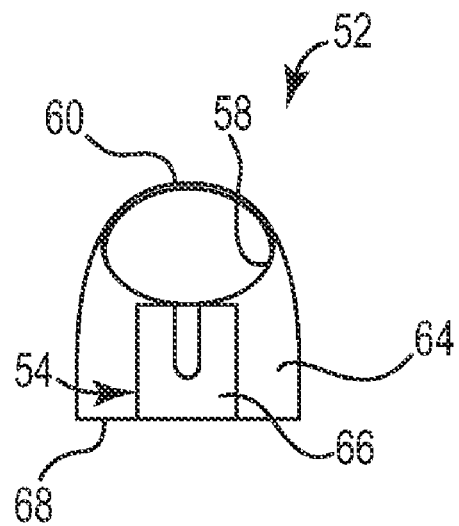
FIG. 3 is a bottom view of the introducer illustrated in FIG. 2.

FIG. 3 is a bottom view of introducer 52 illustrating the U-shaped shelf 66. In one embodiment, shelf 66 extends from a proximal end 68 of introducer 52 up to the window 58. In this manner, delivery device 54 is located proximal of window 58 and does not impede with the window 58 or interfere with the dexterity of the finger pad P (FIG. 1).

Delivery device 54 is suitably fabricated from plastic materials such as polypropylene, polyethylene, silicone, or blends of polyolefin plastics. Delivery device 54 is attached to introducer 52, for example by adhesives, ultrasonic welds, or molding. In one embodiment, introducer 52 and delivery device 54 are formed (molded) as a single integral unit.

Figure 4:
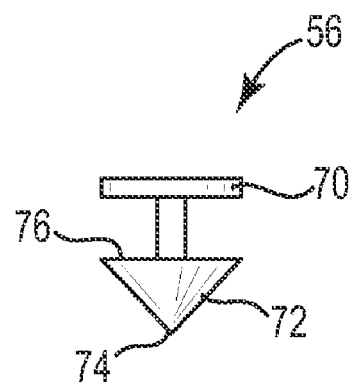
FIG. 4 is a side view of an anchor as illustrated in FIG. 1.

FIG. 4 is a side view of anchor 56. In one embodiment, anchor 56 is provided as a tissue penetrating anchor including a flange 70 and a tissue penetrating barb 72 extending from flange 70. Flange 70 provides an attachment mechanism to removably secure anchor 56 to delivery device 54 (FIG. 2). The tissue penetrating barb 72 includes a leading end 74 configured to penetrate tissue and a trailing end 76 configured to secure barb 72 in the tissue and resist removal of barb 72 from the tissue after placement of anchor 56.

Figure 5:
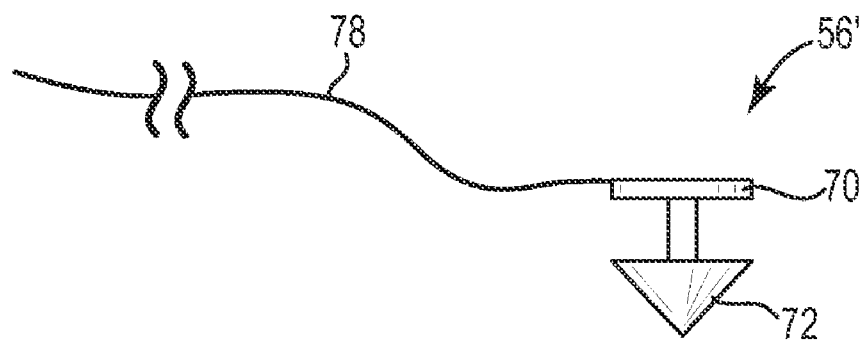
FIG. 5 is a side view of one embodiment of a suture assembly suited for use with the digital suture fixation system illustrated in FIG. 1.

FIG. 5 is a side view of another embodiment of an anchor 56' including a suture line 78 attached to flange 70. In one embodiment, suture line 78 is connected to anchor 56' and provides a pulley line along which support material or other material may be directed along line 78 to the tissue into which anchor 56' is fixed.

In one embodiment, anchors 56, 56' are molded from polypropylene. In one embodiment, anchors 56, 56' are molded from a polymer having a melting point similar to a melting point of suture line 78, which enables suture line 78 to be thermally "welded" to anchors 56, 56'. Suitable suture line materials include suture employed by surgeons in effecting pelvic floor repair, such as polypropylene suture, or the suture identified as Deklene, Deknatel brand suture, as available from Teleflex Medical, Mansfield, Mass., or suture available from Ethicon, a Johnson&Johnson Company, located in Somerville, N.J.

FIGS. 6A-6E illustrate embodiments of system 50 employed in a one-handed method of fixing a suture to tissue of a patient, or more particularly, a method of driving an anchor into tissue of the patient with the same finger that was employed to palpate/identify the target landmark.

Figure 6A:
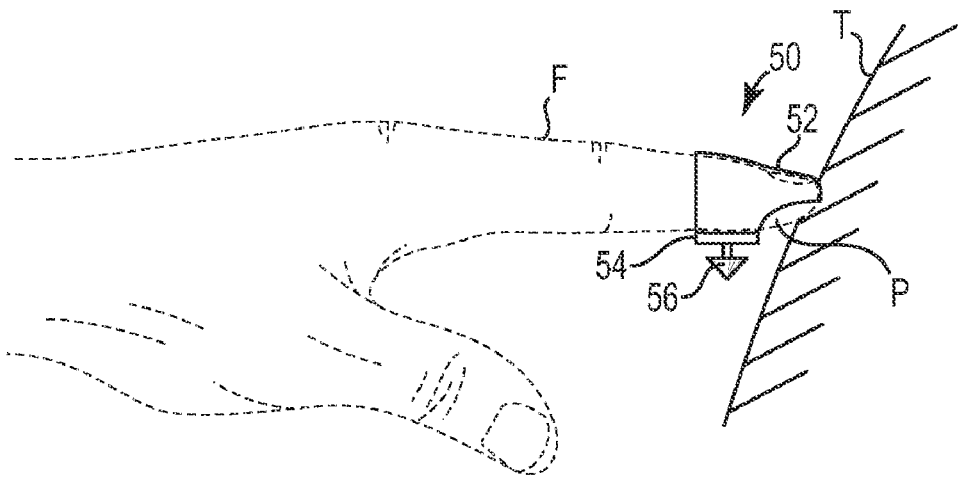
FIG. 6A is a perspective view of a finger wearing the introducer illustrated in FIG. 1 and palpating tissue of a patient.

FIG. 6A is a perspective view of digital suture fixation system 50 placed on the finger F. The pad P of the finger F is exposed in the window 58 of introducer 52 and is available to palpate tissue T of the patient. In one approach, the surgeon will place the introducer 52 onto the finger F, load the anchor 56 into the delivery device 54, and follow a pathway into the tissue that has been previously dissected by the finger F. In this manner, the surgeon is able to identify the desired landmark on the tissue T just prior to deploying the anchor 56.

Figure 6B:
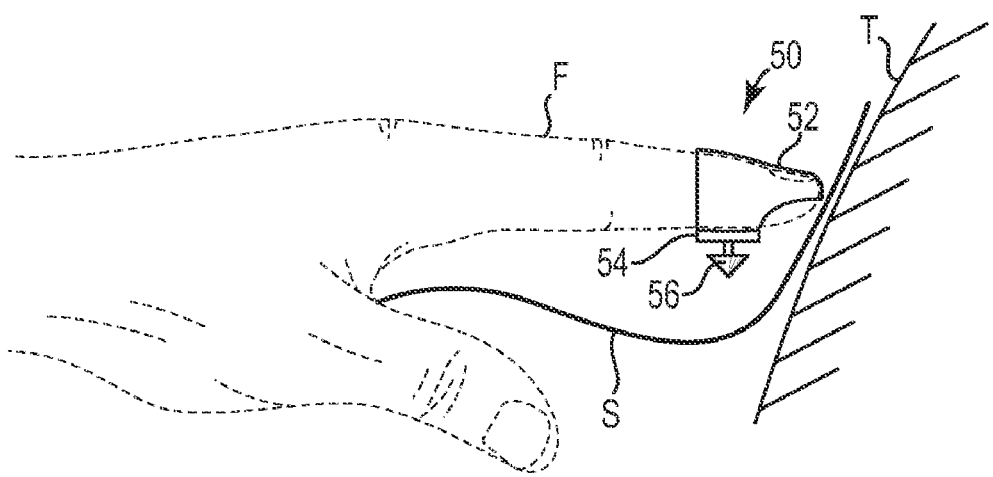
FIG. 6B is a perspective view illustrating the placement of support material between the finger and the tissue of the patient.

FIG. 6B is a side view of a hand of the surgeon holding support material S at the landmark site of the tissue T. Digital suture fixation system 50 is configured to provide the surgeon with dexterity that allows the surgeon to handle and place the support material S at the desired landmark on the tissue T prior to fixing the anchor 56 into the tissue.

The support material S includes materials suited to support the pelvic floor in repair of pelvic organ prolapse. Examples of suitable materials for support material S include synthetic materials, open mesh materials (woven or nonwoven), or biological (harvested tissue) materials. In one embodiment, support material S is provided as a woven polypropylene mesh material available from, for example, HerniaMesh, Chivasso, Italy.

Figure 6C:
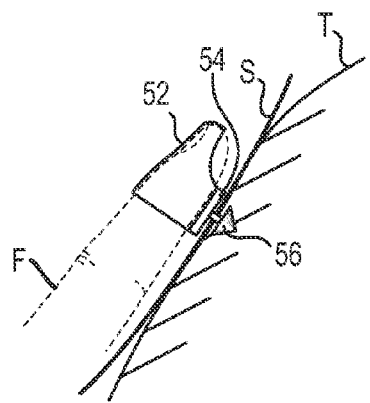
FIG. 6C is a perspective view of the finger illustrated in FIG. 6A inserting an anchor through the support material and into the tissue of the patient.

FIG. 6C is a side view of the finger F employed to insert the anchor 56 through the support material S and into the tissue T. In one embodiment, the delivery device 54 provides a level of rigidity that enables the forceful deployment of anchor 56 through the support material S and into the tissue T. In some instances, the tissue T includes ligaments or other tough, durable connective tissue and the system 50 is compatible with the placement of anchors 56 into these and other tissues.

Figure 6D:
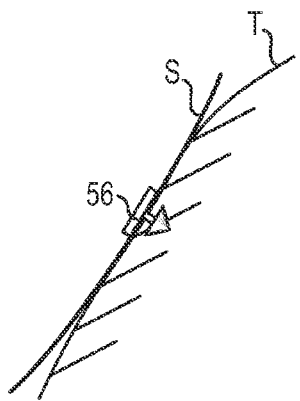
FIG. 6D is a side view of the anchor illustrated in FIG. 6C fixing support material to the tissue of the patient.

FIG. 6D is a side view of anchor 56 fixed into the tissue T to hold support material S in place at the desired landmark as identified by the surgeon.

Figure 6E:
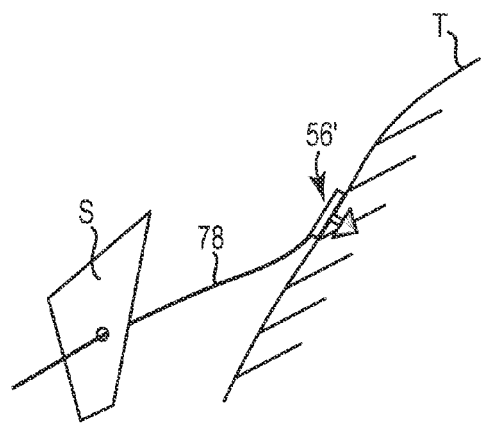
FIG. 6E is a perspective view of one embodiment of support material delivered along a suture line to an anchor that has been placed into tissue.

FIG. 6E is a side view of another embodiment of a suture assembly including suture line 78 attached to anchor 56'. In one embodiment, the support material S is loaded onto or otherwise coupled to a proximal end of the suture line 78 for subsequent delivery along the suture line 78 down to the placed anchor 56'. For example, in one embodiment the anchor 56' is placed in a sacrospinous ligament of the patient and a proximal end of the suture line 78 trails to a location outside of the patient. The surgeon attaches the support material S to the suture line 78 outside of the patient's body and is able to deliver the support material S intracorporeally to the identified landmark where the anchor 56' has been placed. For example, in one approach the surgeon employs a pulley-like motion to move the support material S along the suture line 78 from a location outside of the patient intracorporeally to the anchor fixed in the desired landmark. Thereafter, the surgeon will tie off or otherwise secure the support material S to the tissue T. This approach allows the surgeon to accurately place the support material S intracorporeally at the landmark within the patient without actually visualizing the landmark.

Embodiments of the suturing system and devices described herein provide a method of digitally suturing tissue that is useful in many surgical procedures, including the treatment of pelvic organ prolapse. For example, embodiments provide a suturing system 50 suited for the surgical treatment of pelvic organ prolapse that is operable by a surgeon to suture a scaffold or other support to a ligament or other tissue to reinforce the pelvic floor. With some surgical procedures it is desirable to apply sutures to the sacrospinous ligament and/or in the arcus tendineus ligament to attach a synthetic scaffold thereto that is configured to support the pelvic floor and reduce or eliminate the undesirable effects of pelvic organ prolapse. The digital suture fixation systems described herein are compatible with these approaches to support the pelvic floor.

One embodiment provides a method of fixing a suture to tissue of a patient that includes placing an introducer onto a finger, attaching a suture assembly to the introducer, where the suture assembly has a suture line and an anchor attached to the suture line, delivering the introducer into the patient's body with the finger, and attaching the anchor to the tissue of the patient with the finger.

In a typical procedure related to the repair of pelvic organ prolapse, a catheter is placed in the patient's urethra U, along with other recommended, desirable, and preliminary steps in preparation for surgery. The patient is typically placed on an operating table in a lithotomy position (or modified lithotomy position) with buttocks extending just beyond an edge of the table. With the patient under anesthesia, a vaginal incision or a perineal incision or another suitable incision is made by the surgeon. Thereafter, the surgeon typically dissects tissue using his/her fingers (or a suitable instrument) and then palpates the patient with his/her fingers to identify a desired landmark, such as the sacrospinous ligament or arcus tendineus ligament or other tissue landmark.

The surgeon has thus gained intracorporeal access to the landmark with his/her fingers. The systems described herein allow the surgeon to place an introducer onto a finger and attach a suture assembly to the introducer for direct digital placement of the suture assembly to the landmark. To this end, the surgeon delivers the introducer and anchor into the patient's body with the finger, for example by following the intracorporeal path already dissected through the tissue. The systems thus allow the surgeon, with little additional effort, to attach the anchor to the tissue of the patient digitally with the finger/introducer. In one embodiment, the introducer is placed proximal a distal tip of the finger such that the distal tip of the finger is free to contact the intracorporeal tissue/landmark within the patient. The placement of anchors and/or suture line is repeated in this manner until the surgeon is satisfied with the repair of the pelvic floor.

In one embodiment, a suture line is attached to the deployed anchor and is available for delivering support material intracorporeally to the anchor previously placed in the patient. For example, the proximal end of the suture line is removed from the patient's body to a location where the surgeon may attach support tissue to the suture line. The support material may be accurately placed intracorporeally into the patient (e.g., by a "pulley" method of moving the support material along the suture line) since the distal end of the suture line is attached to the anchor that has already been placed/fixed in the desired landmark.

Figure 7:
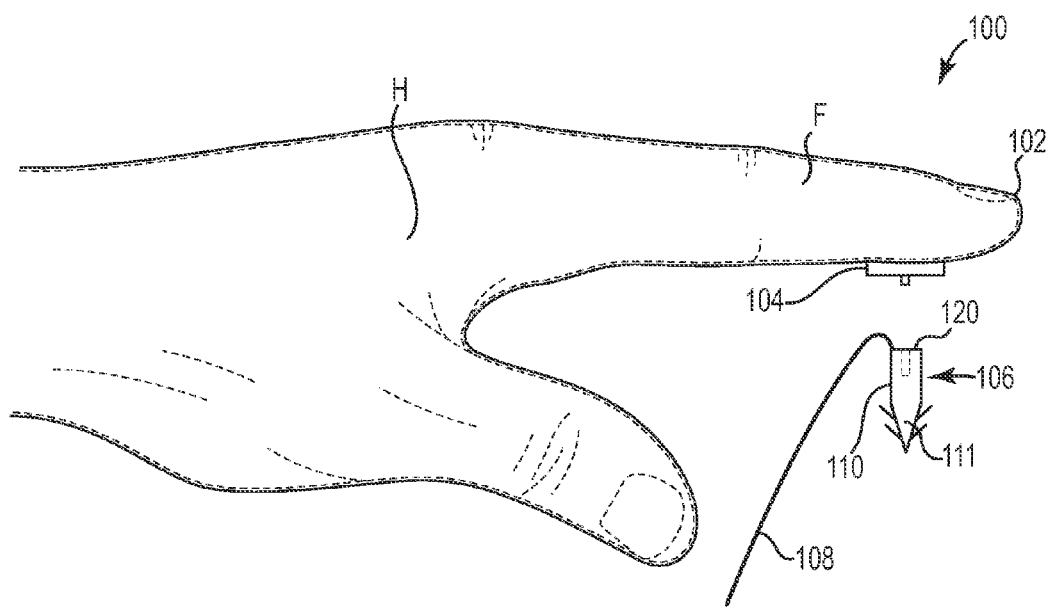
FIG. 7 is a side view of a hand placed inside of a glove that includes a delivery device configured to deliver an anchor intracorporeally into a patient according to one embodiment.

FIG. 7 is a side view of another embodiment of the digital suture fixation system 100. In one embodiment, system 100 includes an introducer 102 that is attachable to a hand H and a finger F of the person, a delivery device 104 attached to the introducer 102, and a suture assembly 106 that is removably attachable to the delivery device 104. In one embodiment, the introducer 102 is provided as a glove that fits over the hand H and the suture assembly 106 includes a suture line 108 connected to an anchor 110.

In one embodiment, the introducer 102 includes a flexible glove such as a nitrile glove or a latex-free glove and the delivery device 104 is provided as a rigid base attached to one of the fingers of the glove. In one embodiment, the glove 102 is fabricated from a polymer having a thin-walled section provided at least at the pad of the finger. As an example, the glove 102 is fabricated from a film having a wall thickness in the region of the pad of less than about 0.005 inches that is suited for providing digital dexterity to the finger.

In one embodiment, anchor 110 is a tissue penetrating anchor provided as a tube including a barb portion 111 opposite a base 120.

Figure 8A:
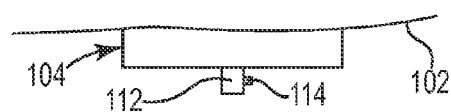
FIG. 8A is a side view of the delivery device and FIG. 8B is a top view of the anchor as illustrated in FIG. 7.
Figure 8B:
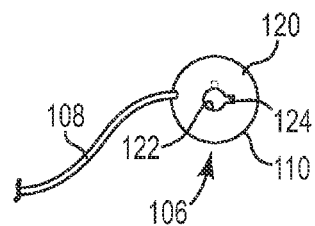

FIG. 8A is a side view of delivery device 104 and FIG. 8B is a top view of suture assembly 106. In one embodiment, delivery device 104 includes a post 112 extending from one of the fingers of the glove 102 and a flange 114 extending from the post 112. In one embodiment, the anchor 110 includes a bore 122 formed in the base 120, where the bore 122 includes a slot 124. In one embodiment, the slot 124 is formed as a helical slot having an entry portion that opens to the base 120 and an end portion located at axial distance away from the base 120 inside of the anchor 110.

The post 112 of the delivery device 104 is sized to fit inside of the bore 122, and flange 114 is sized to mate with the slot 124. Turning the anchor 110 by approximately 90 degrees (i.e., a quarter turn clockwise) secures the anchor 110 to the post 112 by seating the flange 114 in the slot 124. In this manner, anchor 110 is removably secured to the delivery device 104. After placement of the anchor 110 by the hand H inside of the introducer 102, a delivery device 104 is detachable from anchor 110 by turning the delivery device 104 approximately 90 degrees counterclockwise relative to the anchor 110.

In one embodiment, the delivery device 104 is a holder having a first mating surface configured to mate with a second mating surface formed on the base 120 of the anchor 110 such that the holder 104 is configured to decouple from the anchor 110 by separating the first mating surface from the second mating surface. Suitable mating surfaces between the holder 104 and the base 120 include adhesive surfaces, where at least one of the surfaces of the holder 104 and the base 120 is provided with an adhesive; mechanical surfaces such as tongue and groove surfaces as one example; or hook and loop surfaces where one of the surfaces of the holder 104 and the base 120 is provided with a loop structure that mates with a hook structure provided on the other of the holder 104 and the base 120. In one embodiment, the first mating surface of the holder 104 is a convex surface and the second mating surface formed on the base 120 of the anchor 110 is a concave surface, or vice versa.

The suture line 108 is similar to the suture line 78 (FIG. 5). In one embodiment, suture assembly 106 is employed in a manner that is similar to suture assembly 56' (FIG. 5) and provides a trailing suture line 108 that is configured to be directed from the anchor site out of the patient for access by the surgeon, which allows the surgeon to deliver support material S back along the suture line 108 to the landmark inside the patient. Thus, embodiments provide for the placement of support material into a small incision at a desired intracorporeal landmark where the surgeon does not have actual visualization of the landmark.

Embodiments of digital suture fixation systems have been described that include a digital introducer that is attachable to a finger that is used to guide an anchor delivery device intracorporeally to a patient. The introducer is configured to allow the finger to palpate and identify a landmark within a patient and the delivery device is configured to insert an anchor or a suture attached to an anchor into the landmark. Thus, the surgeon's finger is used to deliver the anchor/suture and the space formed in the dissected tissue to locate the landmark may consequently be reduced.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A digital suture fixation system comprising:
   an anchor comprising a leading end configured to penetrate tissue and a trailing end that is configured to resist removal of the leading end of the anchor from the tissue;
   an introducer that is attachable to a finger of a person such that at least a distal tip of the finger is available to palpate tissue and identify a landmark within a patient; and
   a delivery device attached to the introducer, the anchor removably attached to the delivery device;
   wherein the anchor is exposed on an exterior of the delivery device and the delivery device is positioned to allow the finger to push the anchor into the landmark;
   wherein the delivery device comprises a U-shaped dock including a shelf that is spaced away from a surface of the introducer and the anchor comprises a flange configured to be retained between the shelf and the surface of the introducer, the anchor is removable from the dock by sliding the flange past the shelf.

2. The digital suture fixation system of claim 1, wherein the anchor comprises a tissue penetrating barb including the leading end and the trailing end, the tissue penetrating barb extending from a flange, and the anchor further comprising a suture line connected to the flange.

3. The digital suture fixation system of claim 1, wherein the delivery device is configured for one-handed delivery of the anchor into the landmark.

4. The digital suture fixation system of claim 1, wherein the delivery device is operable to push the leading end and the trailing end of the anchor into the landmark.

* * * * *